United States Patent
Tackett

(10) Patent No.: US 6,524,578 B1
(45) Date of Patent: Feb. 25, 2003

(54) USE OF NUCLEASE TO REDUCE WRINKLES AND DISCOLORATIONS IN HUMANS

(76) Inventor: Scott E. Tackett, 1418 Inglenook Dr., Jefferson City, MO (US) 65109

( * ) Notice: Subject to any disclaimer, the term of this patent is extended or adjusted under 35 U.S.C. 154(b) by 1137 days.

(21) Appl. No.: 08/677,838

(22) Filed: Jul. 10, 1996

(51) Int. Cl.⁷ .......................... A61K 38/43; C12N 9/22
(52) U.S. Cl. .................. 424/94.1; 424/94.4; 435/199
(58) Field of Search ................ 424/94.1, 94.4; 435/199

(56) References Cited

U.S. PATENT DOCUMENTS

| 4,376,110 A | | 3/1983 | David et al. |
| 4,535,058 A | | 8/1985 | Weinberg et al. |
| 5,489,524 A | * | 2/1996 | Resnick et al. ............. 435/199 |

FOREIGN PATENT DOCUMENTS

| CA | 1312298 | * | 1/1993 |

OTHER PUBLICATIONS

Pacifici et al. Gerontology 37: 166–180, 1991.*
Article entitled "Mutagenesis in Mammalian Cells Induced by Triple Helix Formation and Transcription–Coupled Repair" by Gan Wang et al., in Science vol. 271, Feb. 9, 1996, p. 802.
Article entitled "Construction of Linkage Maps with DNA Markers for Human Chromosomes" by Ray White et al., in Nature, vol. 313, Jan. 10, 1985, p. 101.

* cited by examiner

Primary Examiner—Mary K. Zeman
(74) Attorney, Agent, or Firm—Haverstock, Garrett & Roberts LLP

(57) ABSTRACT

A method for reducing wrinkles and discoloration on human tissue skin cells which involves forming a nuclease solution and applying the nuclease solution to portions of a subject's body where the subject desires to have wrinkles or discoloration reduced or removed. The nuclease solution is comprised of a nuclease or nucleases, water, and co-factor of nuclease.

1 Claim, 4 Drawing Sheets

(4 of 4 Drawing Sheet(s) Filed in Color)

USE OF NUCLEASE TO REDUCE WRINKLES AND DISCOLORATIONS IN HUMANS

THIS INVENTION

This invention relates to a use of known nucleases mixed in solution to reduce wrinkles and discoloration in humans.

BACKGROUND OF THE INVENTION

In the double-helical structure of DNA, each strand of DNA consists of a backbone of phosphates alternating with ribose or deoxyribose groups. To each ribose or deoxyribose group is attached a base such as adenine or guanine. The two strands of the double helix are held together by hydrogen bonding, i.e., a hydrogen proton on a base attached to one strand is attracted to an electron pair of a corresponding base on the other strand. This attraction is analogous to two ropes, each of which has a series of magnets tied to it; the ropes can be pulled apart temporarily without tearing each magnet off of its rope, and the ropes can subsequently become re-associated via the attraction of the magnets. The two strands of a DNA molecule must be temporarily disassociated from each other in order for vital processes (including replication of DNA to allow cell reproduction, as well as transcription of RNA) to take place.

The process whereby two strands of DNA become hydrogen-bonded to each other is referred to as "annealing." Because of the nature of annealing and hydrogen bonding, two strands of DNA that are not exactly complementary can be attracted to each other and will anneal with a substantial degree of stability under normal (e.g. physiological) conditions. In other words, if two strands of DNA inside a cell have similar but not identical sequences of bases, they can be attracted to each other and anneal. This can lead to various types of DNA recombination. For example, thymine residues can flex somewhat and form hydrogen bonds with guanine residues, even though thymine usually pairs up with adenine. Under in vitro conditions using Southern or Northern blot hybridization, two strands of DNA or RNA can "hybridize" (become annealed to each other, even though they are not perfectly complementary) with as little as 55% homology. Strands with 80% or greater homology can remain attached to each other at temperatures well in excess of 37° C., the normal temperature inside most cells in the human body.

In eukaryotic cells (i.e., cells that have nuclei, such as plant or animal cells) the chromosomes have substantial numbers of repetitive sequences. The highly repetitive sequences are often called the "fast components" of the genome, since they reassociate quickly in vitro after they have been denatured (separated) by means such as boiling. These repetitive sequences are not fully understood; it has been hypothesized that they may be involved in genetic recombination or in regulating gene expression.

Eukaryotic genes also have "introns". These are sequences of DNA in the chromosomal genes which are transcribed into sequences of messenger RNA (mRNA) that are excised, in the cytoplasm, from the primary mRNA transcript before the edited mRNA is translated into protein. Thus, introns are non-translated DNA segments within a gene. Introns (as well as edited mRNA) are eventually digested (i.e., broken down into their building blocks which are called nucleotides, each of which contains a phosphate group, a ribose ring, and a base) in the lysosomes in the cytoplasm, primarily by enzymes called "nucleases".

However, at least some introns either diffuse back into the nucleus or are actively transported into it before they are digested into nucleotides. This is evidenced by the fact that viral nucleic acids, which must pass through the cytoplasm of a cell, quite frequently reach the nuclei of eukaryotic cells.

A nuclease which preferentially digests RNA (i.e., it digests RNA without digesting DNA at a comparable rate) is called an RNase (also capitalized as RNAse); conversely, a nuclease which digests DNA more rapidly than RNA is called a DNase or DNAse. Non-specific nucleases which digest either DNA or RNA at roughly comparable rates are simply called nucleases. A nuclease that digests a DNA or RNA strand at an internal position is an endonuclease. And, a nuclease that digests a DNA or RNA strand on a terminal end is an endonuclease. As used herein, the term "nuclease" includes all five categories of enzymes and combinations of the enzymes.

The terms "polynucleotide" and "oligonucleotide" are used to describe strands of nucleic acids having a sufficient number of bases to anneal with substantial avidity to a strand of DNA or RNA; those terms do not apply to single nucleotides, dinucleotides, or other strands too short to bind with any substantial avidity to a long strand of DNA or RNA having a complementary sequence. Avidity refers not just to the attraction between hydrogen-bonding molecules, but also to their ability to remain coupled together over a prolonged span of time.

As used herein, "non-chromosomal nucleic acids" refers to nucleic acid strands which are inside a living cell, but which are not bonded to the chromosome by a phosphate-sugar bond (i.e., they are not part of either primary strand in a chromosome; however, they might be hydrogen-bonded to one of the primary strands). Non-chromosomal nucleic acids include mRNA, transfer RNA, ribosomal RNA, and introns which have been removed from mRNA. It also includes any other strands of DNA or RNA which are in a living cell but which are not incorporated into a chromosome; this includes DNA or RNA from a virus which has infected a cell, as well as oligonucleotides or polynucleotides generated during digestion or as a result of cell death and lysis, which have been taken up by cells. Once inside the cell, the strands usually are digested further, into single nucleotides that function as metabolites for the cell.

The term "human tissue skin cells" refers to integument or skin cells in a human being and includes the epidermis and dermis layers of skin. The dermis includes the reticular and papillary layers, with the reticular layer including yellow elastic fibers and white tissue.

It has been hypothesized by others that wrinkles are caused by a breakdown in the connective tissue in the skin, typically yellow elastic fibers in the reticular layer of the dermis atrophy. Alternatively, the connective tissue may break down because excess protein produced inside the cells causes the cells to expand, which in turn causes the cells to wrinkle. It is believed that the excess protein that disrupts the connective tissue is produced as a result of oligonucleotides and polynucleotides annealing to the skin cell's chromosome. This causes the regulatory mechanisms on the chromosome to function improperly, and thus proteins are over produced and disproportionately produced. By treating human skin cells with nucleases, protein levels return to close to their original level. Thus, the process either allows the connective tissue proteins to be produced at levels to maintain the skin integrity or decreases the skin cell size or both to reduce wrinkles.

To the best of the Applicant's knowledge, no one has demonstrated an effective method for modifying the entry of non-chromosomal nucleic acids into eukaryotic cells, specifically a method of controlling gene expression in the skin cells, aside from caloric restriction or phlebotomy. Similarly, no one has previously suggested that oligonucleotides and polynucleotides which are taken into skin cells might interfere with the proper functioning of the genes. Finally, no one has suggested that preventing the over-production of protein will prevent the formation of wrinkles and reduce discoloration of the skin.

SUMMARY OF THE INVENTION

This invention involves a method of treating human skin with a solution containing nuclease so that the treatment results in the reduction of discoloration and wrinkles in human skin Specifically, the treatment involves altering the gene expression in human skin cells by means of contacting the skin cells with an effective amount of a nuclease solution containing an exogenous nuclease (an enzyme capable of degrading extra-cellular DNA and/or RNA). The nuclease in the nuclease solution will degrade extra-cellular nucleic acids into nucleotides or oligonucleotides which are too short to have substantial avidity for chromosomal DNA. This in turn will prevent oligonucleotides and polynucleotides from binding to the chromosome in human tissue cells, which prevents the over-production of protein and improper production of protein by individual cells. By altering the production of protein, wrinkles are reduced.

The nuclease solution is applied directly onto the area of the human body where it is desired to reduce wrinkles and discoloration spots, also known as "age spots". The solution may be applied one time or more than one time depending on the size and frequency of the wrinkles and discoloration spots.

The nuclease solution is formed by mixing together water, nuclease co-factor, and at least one nuclease. The nuclease is present in a concentration sufficient to digest at least one molecule of either DNA or RNA.

DRAWINGS

The file of this patent contains at least one drawing executed in color. Copies of this patent with color drawing(s) will be provided by the Patent and Trademark Office upon request and payment of the necessary fee.

DESCRIPTION OF THE PREFERRED EMBODIMENTS

Figure 1:
FIG. 1 is a photograph of a sixty-four year old female before treatment with the solution of the claimed method.

The present invention is for a method for reducing skin wrinkles and skin discoloration, such as "age spots", on a human being which works by applying a solution containing a nuclease to the surface of a human subject's skin. The nuclease solution is comprised of water, at least one nuclease, and a co-factor capable of activating the nuclease.

Also incorporated herein as non-essential material for purposes of indicating the background of the invention and illustrating the state of the art is Canadian Patent No. 1,312,298, which was invented and is owned by the inventor of the present invention.

The method of the present invention is used to apply a nuclease solution to a subject's skin, with the method summarized as follows, a nuclease solution is prepared and the nuclease solution is then applied to a human subject's skin to reduce wrinkles and discoloration spots. The method is initiated by first preparing the nuclease solution and then placing the nuclease solution in a delivery device which will allow the nuclease solution to contact the skin of the subject being treated. Preferably, the delivery device allows the subject to accurately place the nuclease solution where the subject desires. Typically, the delivery device used is either a wash cloth or similar type device which allows the nuclease solution to contact the skin without dissipating away from the desired area of contact. Also, an ice cube may be used to deliver the nuclease solution to the desired area. Finally, a delivery device does not have to be used, instead the nuclease solution can be applied directly on the subject. Thus, the nuclease solution is prepared and then placed on the area where the subject desires to have wrinkles and discoloration reduced. The method for reducing wrinkles and discoloration may be used once or a number of times depending upon the size and frequency of the wrinkles and discoloration.

The nuclease solution discussed herein is formed by combining an amount of water capable of effectively covering a desired portion of skin, with an effective amount of nuclease of sufficient concentration to readily digest extra-cellular DNA and/or RNA, and an effective amount of nuclease co-factor sufficient to activate the nuclease. Once the nuclease, water, and co-factor are combined, they are mixed and placed on a body area on a human subject. Where the solution is placed will depend upon where wrinkles or discoloration exist on the human and which wrinkles or discolorations the individual prefers to have reduced.

The most preferred nuclease composition used in the present method contains approximately 500 milliliters of water, approximately 60 grams of co-factor, preferably magnesium sulfate, and approximately 15,000 Kunitz units of DNase and 10,000 Kunitz units of RNase. The 60 grams of magnesium sulfate will form a one molar solution of magnesium sulfate in water. As mentioned, the solution may be applied directly to a human subject by using either a wash cloth or similar device which holds the nuclease solution and can be placed directly onto a subject's skin, whereby the solution is in contact with the subject's skin. Any other method of applying the nuclease solution to the subject's skin may be used as long as the nuclease is not degraded to the point that it will not adequately digest DNA and/or RNA. The amount of nuclease solution applied to a subject's skin may range between about 0.01 milliliters of nuclease solution per square centimeter of skin to about 10 milliliters of nuclease solution per square centimeter of skin. Additionally, the nuclease solution will be applied such that between about 1 Kunitz unit and about 50,000 Kunitz units of nuclease will be applied to each square centimeter of skin contacted by the nuclease solution. It is important to remember, however, that the activity of the nuclease is important, because that activity of the nuclease will generally determine the concentration of the nuclease applied. Thus, if a nuclease has higher activity, a lesser concentration of nuclease may be applied to accomplish the same result.

Further, it is possible to apply the nuclease enzyme directly to the skin of a subject without blending the nuclease into solution. This would work because the skin already contains some co-factor and water. While the nuclease solution is the most preferred way of contacting the nuclease with the skin it may be possible to apply the nuclease separately without solution.

Generally, any type of water is acceptable for use in the solution used in the process to reduce wrinkles. The water is important to the nuclease solution because not only does it provide a medium for forming a solution but, more importantly, the water provides a substance that oligonucleotides and polynucleotides can migrate into from the cytoplasm of a cell. When the skin cells are contacted by the nuclease solution, oligonucleotides and polynucleotides will migrate out of the cell's cytoplasm, through the cell wall, and into the nuclease solution. Also, the water will contact and mix with the extra-cellular fluid that is located between some of the skin cells.

The amount of water used is dependent upon the amount of skin that must be covered by the nuclease solution. Thus, the amount of water used is only limited by the amount of nuclease and co-factor available to the user of the solution, and the amount of skin to be contacted by the solution. Consequently, the amount of water used may vary from approximately a single drop or around one half milliliter to a bathtub full of water or around ten liters. Water may be added to a subject's treated skin to keep the skin damp and the reaction running.

Any nuclease, that is capable of degrading oligonucleotides and polynucleotides present in the cytoplasm of human skin cells, may be used. It is desirable to use a combination of nucleases so that both RNA and DNA oligonucleotides and polynucleotides present in the cytoplasm and extra-cellular fluid will be digested. The oligonucleotides and polynucleotides will migrate from the cytoplasm to the extra-cellular fluid and nuclease solution. The migration occurs as a result of diffusion under the gas law. Thus, a concentration gradient is created whereby the oligonucleotides and polynucleotides present in the cell's cytoplasm will diffuse into the extra-cellular fluid or nuclease solution because the extra-cellular fluid and nuclease solution contain a lesser concentration of oligonucleotides and polynucleotides. Also, the nucleotides will continue to migrate out of the cytoplasm as the concentration of oligonucleotides and polynucleotides drops in the extra-cellular fluid and nuclease solution. Thus, when choosing a nuclease it is important to use a nuclease that not only sufficiently degrades or breaks up large fragments of DNA and/or RNA, but also to choose a nuclease or combination of nucleases that will break-up both DNA and RNA oligonucleotides and polynucleotides.

The most preferred nuclease solution uses a combination of both Deoxyribonuclease and Ribonuclease so that fragments of both RNA and DNA are attacked and digested. If only DNase is used, the RNA which is hydrogen bonded to the chromosome may inhibit the removal of DNA from the chromosome. If only RNase is used, DNA may inhibit the removal of RNA from the chromosome.

The concentration of the nuclease used in the nuclease solution will generally range between a total concentration equal to from about 1 Kunitz unit to about 50,000 Kunitz units per human subject. However, there may be no upper limit to the amount of nuclease used, as using more nuclease may not significantly increase the rate of reaction. More preferably, the amount of nuclease used is a concentration of from about 1 Kunitz unit/milliliter of water to about 70 Kunitz units/milliliter of water. Furthermore, the nuclease solution may be applied to a subject in an amount equal to from about 0.5 milliliters of nuclease solution per square centimeter of skin to about 10 milliliters of nuclease solution per square centimeter of skin. A Kunitz unit is a unit of activity which results in the degradation of either DNA or RNA at a specified temperature and within a specified period of time. The more preferred concentration of nuclease in solution will be equal to an amount of Ribonuclease equal to from about 1 Kunitz unit to about 20,000 Kunitz units or between about 1 milligram and about 200 milligrams of Ribonuclease per liter of water and an amount of Deoxyribonuclease equal to a concentration of from about 1 Kunitz unit to about 30,000 Kunitz units or between about 1 milligram and about 50 milligrams of Deoxyribonuclease per liter of water. Some nucleases will have a higher concentration of activity or Kunitz units per milligram of protein than other nucleases. This means some nucleases degrade the DNA or RNA faster. Because the activity may be varied, the concentration of nuclease may differ from the above disclosed amounts. The most preferred activity is for a Ribonuclease to have an activity equal to about 100 Kunitz units per milligram of protein and for the Deoxyribonuclease to have an activity equal to about 1,500 Kunitz units per milligram of protein.

It is preferable to include a co-factor in the solution, as the co-factor is required to activate the DNase and may be required to activate the RNase. Without the co-factor the DNase will be unable to digest strands of DNA and/or RNA. Any co-factor may be used that is capable of activating the DNase. Typically, the preferred co-factor is a magnesium salt selected from the group consisting of magnesium chloride, magnesium phosphate, magnesium sulfate, and magnesium nitrate. The amount of co-factor used generally ranges between about 4.2 microMoles and about 2 Moles, with the most preferred concentration of co-factor equal to about 1 Mole.

Thus, the inventive process comprises the step of treating skin cells with a nuclease solution comprised of an exogenous nuclease added to a water solution. When the nuclease solution is placed on the surface of the skin it is in fluid communication with the skin cells, so that the exogenous nuclease migrates into the extra-cellular fluid or remains in the nuclease solution under suitable conditions and for an adequate period of time to allow the exogenous nuclease to digest extra-cellular oligonucleotides and polynucleotides which migrate into the extra-cellular fluid or nuclease solution. The exogenous nuclease will digest extra-cellular polynucleotides and oligonucleotides into nucleotides or oligonucleotides which are too short to bind with substantial avidity to the chromosomal DNA. This effectively alters the diffusion and uptake of extracellular oligonucleotides and polynucleotides into the cells, thereby altering the concentration and distribution of oligonucleotides and polynucleotides inside the cells which are bound to the chromosomes of the cells by hydrogen bonding.

The process of this invention does not lead to the alteration of the DNA in the main strands of the chromosomal double helices. Instead, this process can be roughly summarized by the phrase, "cleaning the chromosomes." The nuclease treatment of this invention alters the distribution of oligonucleotides and polynucleotides in the extra-cellular fluid and cytoplasm of the cell, which are generated by various processes such as digestion, cell death and lysis, etc. Extra-cellular oligonucleotides and polynucleotides can diffuse or be actively transported into cells, since they normally serve as nutrients once they enter a cell. However, the inventor has discovered that such oligonucleotides and polynucleotides, if they remain in relatively long strands, apparently can diffuse or be transported through the cytoplasm and into the nuclei of eukaryotic cells, including skin cells. After they reach the nuclei, the exogenous strands can anneal to single strands of DNA that become exposed when a segment of DNA temporarily opens up to allow for transcription, replication, or other processes.

When an exogenous polynucleotide or oligonucleotide anneals to an exposed single strand of chromosomal DNA, the semi-complementary polynucleotide or oligonucleotide binds to the chromosomal strand less tightly than the fully-complementary chromosomal strand would binds but still tightly enough to remain attached for some period of time. In a sense, the exogenous polynucleotide creates a "pseudo-strand" that binds to and entangles one of the strands of the chromosomal DNA, preventing that strand from returning to the double helical configuration with its fully complementary true chromosomal strand. In that manner, the pseudo-strand interferes with the proper functioning of any genes that are contained within or affected by the region of DNA that is entangled by the exogenous polynucleotide.

The problem of pseudo-strand interference remains unless and until the exogenous polynucleotide or oligonucleotide is removed somehow; however, the process of removal might never happen in a particular cell. A gene might remain entangled and encumbered by the exogenous polynucleotide until the cell or the organism that contains the cell eventually dies.

Alternatively, an exogenous polynucleotide or oligonucleotide might be substituted for the original DNA sequence. This process would involve several steps, including (1) the annealing of an exogenous strand to an exposed semi-complementary single strand of chromosomal DNA, followed by (2) the mistaken excision of the proper strand by a chromosomal repair mechanism which cannot properly distinguish between the proper strand and the pseudo-strand, followed by (3) the generation of a second strand of DNA which is incorporated within the chromosome, to match the exogenous strand. In this process, the exogenous strand would displace and eliminate the proper gene.

Even if an exogenous pseudo-strand is recognized as exogenous and is removed and digested into nucleotides by some chromosomal repair mechanism, the proper expression of the affected gene(s) will be inhibited for as long as it takes for the repair mechanism to recognize and get rid of the exogenous strand.

The subject inventive method centers around the following discovery: by digesting exogenous oligonucleotides and polynucleotides while they are in the extra-cellular fluid or after they have migrated into a nuclease solution from a cell's cytoplasm, it is possible to alter the presence and distribution of exogenous oligonucleotides and polynucleotides inside the cells. That process, in turn, alters the rate or quantity of hydrogen binding of exogenous oligonucleotides and polynucleotides to the chromosomes of the cells. The process is in essence a two part process whereby the exogenous nuclease degrades extra-cellular polynucleotides and oligonucleotides, which leads to a change in equilibrium between the extra-cellular polynucleotides/oligionucleotides and the intra-cellular polynucleotides/oligionucleotides, resulting in a passage of nucleotides from the cytoplasm of the cell to the extra-cellular fluid. Once this occurs there is a change in equilibrium between the non-chromosomal nucleotides, attached to the chromosome in the nucleus, and the nucleotides present in the cell's cytoplasm, which results in the passage of the non-chromosomal DNA and RNA from the nucleus, where it was hydrogen bonded to the chromosome, to the cytoplasm of the cell. Therefore, treatment with exogenous nucleases causes an alteration in the amount and type of protein produced in the "cleaned" cells. By "cleaning the chromosomes" (or, more precisely, by preventing them from becoming entangled by unwanted exogenous polynucleotides and oligonucleotides), proper gene expression is protected and enhanced. By preventing improper gene expression the amount of improper protein produced is limited. Because the amount of protein improperly produced is reduced it is theorized that this reduces the aging of cells. By reducing the aging of cells this prevents the breakdown of the skin tissue and thus prevents the formation of wrinkles.

As used herein, the term "nuclease" refers to an enzyme or enzymes capable of degrading extra-cellular DNA and/or RNA. An "exogenous" nuclease refers to a nuclease originally produced by cells other than the cells being contacted, and to nuclease produced by artificial means such as peptide synthesis or chemical alteration of a different enzyme.

The phrase, "altering the gene expression" refers to changes which are observable using available methodology. Such changes may involve phenotypic alternations such as cell or culture morphology, pH of cell metabolites or cell culture fluids, expression of one or more observable polypeptides, etc., or they may involve genotypic alternations observable by means of DNA or RNA hybridization using Southern or Northern blots or similar methods.

The phrase, "contacting the cells with an exogenous nuclease for the purpose of digesting extra-cellular nucleic acids" does not include cell and nuclease contacts which are merely incidental to other intended purposes. For example, whenever a cell dies, it releases nucleases which had been digesting mRNA into nucleotides within that cell's own cytoplasm. Such release is merely incidental, and is not included within the cited phrase.

The inventive process disclosed herein is not gene-specific genetic engineering, instead the process is used to remove unwanted oligonucleotides and polynucleotides from the cell's chromosome. The treatment can be used on any culture of human tissue skin cells, and the actual effects can be determined by visually observing the treated cells, as is shown in the accompanying photographs. It has been observed that use of the present process will not only reduce wrinkles and discoloration on human subjects, but increase hair growth in those areas treated with the process disclosed herein. The process in essence results in the cells being more efficient and prevents them from producing unneeded and undesirable proteins. This in turn results in less degradation of surrounding tissues, more efficient growth of surrounding tissues, and in essence a reversal of the aging process, which is hypothesized to be the result of the accumulation of unwanted proteins within the cells.

EXAMPLES

Example 1

The inventive method using a nuclease solution to reduce wrinkles in a human.

A 500 milliliter (ml) solution of 1 molar magnesium sulfate ($MgSO_4$) was prepared by adding 60 grams of magnesium sulfate to 500 ml of tap water. Added to the 500 ml of 1 molar magnesium sulfate was 15,000 Kunitz units (Ku) of DNase, more specifically Deoxyribonuclease 1 manufactured by Sigma Chemical Company of St. Louis, Mo., having a product index number of D-5025 and having an activity of 1,500 Ku/mg protein wherein the Kunitz unit is a unit of enzyme activity wherein the unit is defined so that one Kunitz unit will produce a $\Delta A_{260}$ of 0.001 per min per ml at pH 5.0 at 25° C., using DNA Type I or III as a substrate. Also added to the 1 molar solution of magnesium sulfate was 10,000 Ku of RNase, more specifically Ribonuclease A manufactured by Sigma Chemical Company of St. Louis, Mo., having a product index number of R-5125, with the RNase having an activity equal to approximately 100 Ku/mg of protein wherein the Kunitz unit is a unit of activity defined so that one Kunitz unit will produce a $\Delta A_{260}$ of 1.0 in 30 minutes at pH 7.5 at 37° C. in a 1.5 ml reaction volume with a substrate which is yeast RNA. The magnesium sulfate was added because it is a co-factor of DNase. The nuclease solution having 60 grams of magnesium sulfate, 15,000 Kunitz units of DNase and 10,000 Kunitz units of RNase in 500 milliliters of water will be referred to as "stock solution".

The stock solution of magnesium sulfate, water, RNase, and DNase was thoroughly mixed and then placed on a subject, which was a 41 year old male. The solution was applied primarily around the eye sockets of the subject as well as the remainder of the subject's body, including the scalp. The solution was allowed to evaporate from the subject's body, with the evaporation of the water from the solution taking approximately 35 minutes. The skin was kept damp with water for another 15 minutes. The solution was then completely removed after 50 minutes by having the subject bathe in a shower, thereby rinsing the dried nucleases off the subject's body.

Approximately, 2 months after the first treatment a second treatment of the subject was made.

A solution of 500 ml of stock solution was prepared. The solution was thoroughly mixed to readily disperse the nucleases within the magnesium sulfate solution. After mixing, 250 milliliters of the stock solution was placed on the subject in the same manner as before. The solution was left on the subject for approximately three (3) hours. The skin of the subject was kept damp with water for a three (3) hour time period to facilitate the process. The solution was then removed like before, by having the subject bathe.

It was visually observed after the first and the final treatment that the wrinkles near the subject's eye sockets had been significantly reduced, so that upon visual observation the wrinkles around the subject's eye sockets were not visible to the naked eye. Thus, the use of the nucleases in solution resulted in the reduction of the subject's wrinkles.

Also, it appeared that the subject's hair grew at a rate of around twice the normal rate. The subject's hair typically grew at a rate of ¾ of an inch to 1 inch during a six week time span. After treatment with the nuclease solution the subject's hair grew 1.5 inches in six weeks. This is a significant increase that shows that the process increases the efficiency of cellular activity such as hair growth.

Example 2

500 milliliters of stock solution was prepared according to the method detailed in Example 1. The solution was thoroughly mixed to readily disperse the nucleases within the magnesium sulfate solution.

250 milliliters of the stock solution was then placed on a 64 year old female subject for 50 minutes, with the solution placed on the subject's face, neck, and arms. The solution was then washed off using a shower, which removed non-absorbed and extraneous nucleases.

Figure 2:
FIG. 2 is a photograph of the sixty-four year old female of FIG. 1 after treatment with the solution of the claimed method.
Figure 3:
FIG. 3 is a close-up photograph of the sixty-four year old female of FIG. 1 after treatment with the solution of the claimed method.

The subject visually noticed a significant reduction in the wrinkles around the subject's eye sockets as well as a tightening of skin on the subject's neck and arms. Furthermore, this visual evidence is shown by the included photos which show the subject's face before and after treatment with the claimed solution. FIG. 1 is the subject before treatment and FIG. 2 is the subject after treatment. As can be seen after treatment with the present process the subject showed a significant decrease in the number of wrinkles around the subject's eye sockets. FIG. 3 is even more revealing as it is a close-up photograph of the 64 year old subject's face. As can be seen the subject's wrinkles are virtually gone. Further, when FIG. 3 is compared to FIG. 1 there is a pronounced difference between the size and number of wrinkles on the subject's face before and after treatment. FIG. 3 shows that the method of the claimed invention reduces wrinkles.

Example 3

A solution of 500 ml of stock solution was prepared according to the method of Example 1. The solution was placed on the hand of a 77 year old male for approximately 15 minutes, more specifically the solution was placed on an "age spot" on the hand of the subject. After the passage of 15 minutes the solution was then washed off using a water faucet. The male observed that the size of the age spot was reduced after treatment with the present method. This verifies that the method results in the reduction of discoloration spots on humans.

Example 4

A 500 ml solution of stock solution was prepared according to the method of Example 1. 250 ml of the stock solution was then placed on an ice cube tray having 14 receptacles so that approximately 18 ml of stock solution was present in each receptacle to form 14 ice cubes containing approximately 18 ml of stock solution. 18 ml of the stock solution is roughly equivalent to one twenty-eighth (⅟28) of the 500 ml of stock solution. Also, the stock solution ice cubes had approximately 535.7 Kunitz units of DNase and 357 Kunitz units of RNase. Thus, the 500 ml of stock solution formed a total of 28 ice cubes with each containing 535.7 Kunitz units of DNase and 357 Kunitz units of RNase. One ice cube was used on a 43 year old female subject, wherein the subject rubbed the ice cube on the subject's face until the ice cube had melted. The solution was then washed off approximately 15 minutes after the ice cube had melted. This treatment was repeated the following day using another ice cube containing RNase and DNase. Again, the ice cube was rubbed on the subject's face until the ice cube had completely melted and the solution was again washed off after approximately 15 minutes.

After the passage of two (2) days since the last treatment the subject noticed a significant tightening of the skin and also a reduction in the size of the wrinkles on the subject's face. Again these claims are substantiated by the before and after photographs included herewith.

Figure 4:
FIG. 4 is a photograph of a forty-three year old female before treatment with the solution of the claimed method.
Figure 5:
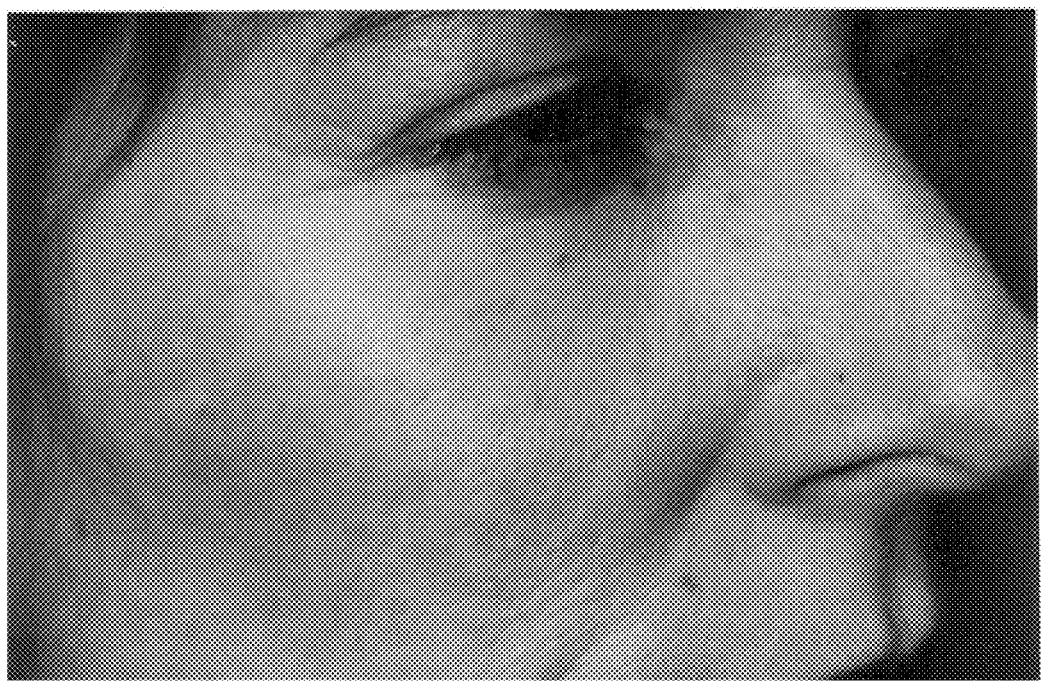
FIG. 5 is a close-up photograph of the forty-three year old female of FIG. 4 before treatment with the solution of the claimed method.
Figure 6:
FIG. 6 is a close-up photograph of the forty-three year old female of FIG. 4 after treatment with the claimed solution of the claimed method.
Figure 7:
FIG. 7 is a close-up photograph of the forty-three year old female of FIG. 4 after treatment with claimed solution of the claimed method.

FIGS. 4 and 5 show the subject before treatment. FIG. 5, in particular, shows wrinkles around the subjects eye. FIGS. 6 and 7 are taken two days after the last treatment. As can be seen, the subject shows a significant reduction in wrinkles around the eye. FIG. 7 when compared to FIG. 5 shows a significant difference between the skin before and after treatment. It is believed that the method used on the subject resulted in a reduction in the size of wrinkles.

Thus, there has been shown and described a novel method for reducing the size of wrinkles and discoloration on a human subject, wherein the method uses a nuclease solution comprised of water, nuclease, and co-factor of nuclease which fulfills all of the objects and advantages sought therefore. It will be apparent to those skilled in the art, however, many changes, variations, modifications, and other uses and applications for the subject method are possible, and all such changes, variations, modification, and other uses and applications which do not depart from the spirit and scope of the invention are deemed to be covered by the invention which is limited only by the claims which follow:

What is claimed is:

1. A method for reducing wrinkles and discoloration in humans which comprises the step of applying to human tissue skin cells an effective amount of a nuclease solution, said nuclease solution comprised of:

(a) water;
   (b) an amount of nuclease equal to from about 1 Kunitz unit per millimeter of water to about 70 Kunitz units per milliliter of water, and
   (c) a co-factor capable of activating the nuclease,
      wherein said nuclease solution is applied on a subject's skin in an amount equal to from about 0.01 milliliters of said nuclease solution per 1 square centimeter of skin to about 1 milliliter of said nuclease solution per 1 centimeter of skin, and
      wherein after application of said nuclease solution wrinkles and discolorations are reduced in humans.

* * * * *